United States Patent
Downie et al.

(10) Patent No.: US 7,431,033 B2
(45) Date of Patent: Oct. 7, 2008

(54) GAS DISPENSING AND RECOVERY APPARATUS

(75) Inventors: Neil Alexander Downie, Guildford (GB); Stuart Alexander Kerr, Knutsford (GB)

(73) Assignee: Air Products and Chemicals, Inc., Allentown, PA (US)

( * ) Notice: Subject to any disclaimer, the term of this patent is extended or adjusted under 35 U.S.C. 154(b) by 430 days.

(21) Appl. No.: 10/512,734

(22) PCT Filed: May 1, 2003

(86) PCT No.: PCT/GB03/01883

§ 371 (c)(1),
(2), (4) Date: Jan. 9, 2006

(87) PCT Pub. No.: WO03/093722

PCT Pub. Date: Nov. 13, 2003

(65) Prior Publication Data

US 2006/0144225 A1 Jul. 6, 2006

(30) Foreign Application Priority Data

May 1, 2002 (GB) .................................. 0210022.0

(51) Int. Cl.
*F17C 7/00* (2006.01)
*A61M 16/00* (2006.01)

(52) U.S. Cl. ............................. 128/204.18; 128/205.15; 222/105; 222/389

(58) Field of Classification Search ...................... 95/90; 96/4, 108; 128/203.12, 204.18, 205.13, 205.15; 222/92, 206, 209, 105, 386.5, 389; 220/495.01–495.11; 138/30

See application file for complete search history.

(56) References Cited

U.S. PATENT DOCUMENTS

| | | | | |
|---|---|---|---|---|
| 4,636,226 A | * | 1/1987 | Canfora | 95/138 |
| 4,869,733 A | * | 9/1989 | Stanford | 95/19 |
| 5,622,282 A | * | 4/1997 | Yazawa et al. | 222/95 |
| 6,213,120 B1 | * | 4/2001 | Block et al. | 128/204.23 |
| 6,990,979 B2 | * | 1/2006 | Koch | 128/204.13 |

FOREIGN PATENT DOCUMENTS

| | | | |
|---|---|---|---|
| DE | 10021289 A1 | * | 11/2001 |
| EP | 769304 A1 | * | 4/1997 |
| EP | 1041337 A1 | * | 10/2000 |

* cited by examiner

*Primary Examiner*—Frank M Lawrence
(74) *Attorney, Agent, or Firm*—Willard Jones, II

(57) ABSTRACT

A container (1) having a first compartment (3) and a second compartment (5) separated by a movable gas impermeable partition (7) is used for storing and dispensing a gas for use in a process and receiving and storing a gas recovered from the process. Fresh gas is dispensed (9) from the first compartment (3) for use in a process and recovered gas is fed (11) to the second compartment (5), whereby a volume of the second gas displaces a volume of the first gas by movement of the partition (7) to enlarge the second compartment (5) relative to the first compartment (3).

16 Claims, 2 Drawing Sheets

GAS DISPENSING AND RECOVERY APPARATUS

The present invention relates to a process of and an apparatus for use in containing and dispensing gas and storing recovered gas.

More particularly the present invention relates to a container having two compartments divided by a flexible partition means, wherein the first compartment may be charged with a fresh gas and the second compartment may be charged with recovered gas used in a process for which the fresh gas was provided, such that the pressure of recovered gas may, at least partially, provide the driving force for dispensing the fresh gas and where the recovered gas may displace the fresh gas in the container. The invention further relates to a process for the dispensing and recovery of gas using such apparatus.

Containers having two compartments separated by a flexible partition are known, where a first compartment contains a liquid and a second compartment contains a propellant gas.

For example, in the brewing industry a container having a strong rubber or polypropylene outer jacket having a flexible internal bag of heavy gauge metal foil with a dual plastic coating is used. In use, the flexible inner bag contains beer which is dispensed via a tap or valve and the ullage space of the outer jacket is charged, via a charging valve, with a propellant gas such as compressed air or carbon dioxide. Thus the pressure of gas in the ullage space drives the dispensing of the beer in the flexible bag when the dispensing valve is open.

U.S. Pat. No. 5,622,282 (Yazawa et al) discloses a double-wall aerosol container comprising a metallic outer jacket and a generally tubular flexible inner bag for containing the aerosol. The space between the outer jacket and the flexible inner bag provides a space in which the aerosol propellant may be charged via a charging valve at the base of the outer jacket. A housing integrates the outer jacket and the aerosol-containing inner bag with a dispensing valve mechanism such that the aerosol may be dispensed through a dispensing valve by depressing a stem; the aerosol being driven through the valve by the pressure of the propellant in the outer jacket. During manufacture, once the container has been assembled, aerosol content may be charged into the inner bag via the dispensing valve stem and then the propellant charged into the outer jacket via the charging valve.

EP-A-1041337 (Mannesmann) discloses a pressurized gas container for containing gaseous fuel for a vehicle and having two variable capacity compartments separated by a gas-tight flexible partition made of a low thermal conductivity material. Pressurized gaseous fuel is first filled into a first of the compartments from a larger pressurized container at a gas station until the maximum, or a predetermined, temperature and pressure of the gas in the fist compartment is reached. The second compartment is then filled with gas whilst at the same time removing gas from the first compartment by suction. The initial warm-exchange fill into the first compartment has the effect of allowing a greater pressure of cooled gas to be fed into the container.

Hypodermic injection devices, such as that disclosed in U.S. Pat. No. 6,258,063, include a medication unit (a first container) which is typically made of easily deformed material such as plastic or metal foil and contains the medication to be expelled through an exiting orifice. The driving force is provided by the gas pressure in the surrounding container, generated by, for example, rapid combustion of an explosive substance. A high pressure liquid jet of medication for transdermal administration can thereby be generated.

A process for dispensing fresh gas and receiving recovered gas and an apparatus for use in such a process is desirable, particularly where the gas is a high value gas and especially where the processing apparatus to which the fresh gas is provided is in an environment where space is at a premium.

Accordingly, in a first aspect of the invention, there is provided a method of storing and dispensing a first gas for use in a process and receiving and storing a second gas, said method comprising the steps of storing the first gas in the first compartment of a container having a first compartment and a second compartment separated by a movable gas impermeable partition, dispensing the first gas from the first compartment of the container via a gas outlet of the container and providing the first gas to a processing apparatus for carrying out a process involving the first gas; recovering gas from said processing apparatus; and feeding at least a portion of said recovered gas to the second compartment of the container via a gas inlet of the container to provide at least a portion of the second gas, whereby a volume of the second gas displaces a volume of the first gas by movement of the partition to enlarge the second compartment relative to the first compartment.

In a second aspect of the invention, there is provided use of a container for storing and dispensing a gas for use in a process and receiving and storing a gas recovered from the process, wherein the container comprises a first compartment having a gas outlet and a second compartment having a gas inlet, said first and second compartments separated by a gas impermeable partition, wherein said partition is moveable such as to enable the relative volumes of the first and second compartment to be varied.

In a third aspect of the invention, there is provided apparatus for storing and dispensing a gas for use in a process and receiving and storing a gas recovered from the process, said apparatus comprising a container, which container comprises a first compartment for containing a first gas and having a gas outlet; a second compartment for containing a second gas and having a gas inlet; and a gas impermeable partition which separates the first compartment and the second compartment, wherein said internal partition is moveable such as to enable the relative volumes of the first and second compartments to be varied; a processing apparatus for carrying out a process involving a gas; a dispensing conduit for feeding gas from the gas outlet to the processing apparatus; a recovery conduit for feeding gas from the processing apparatus to the gas inlet; and a pumping means for pumping the gas from the processing apparatus into the second compartment.

Usually, the container will be rigid and hence of fixed overall volume; i.e. the sum of the volumes of the first and second compartments will be constant irrespective of the relative size of those compartments.

It will be understood that the volume of the first compartment displaced by the recovered gas depends upon relative mass of gas in the two compartments. For example, if 10 liters NTP of fresh gas is dispensed from the first compartment of a container having a total volume of 10 liters and containing only fresh gas at 10 bar in the first compartment (i.e. empty second compartment), the pressure in the container will fall to 9 bar. If 5 liters NTP of recovered gas is then fed into the second compartment, the volume of that compartment will increase (from 0) to 0.5 liters with a corresponding 0.5 liter decrease in volume of the first compartment, because the pressure within the container will increase (from 9) to 9.5 bar. If a further 45 liters of NTP fresh gas is then dispensed, the pressure within the container will fall to 5 bar, causing the volume of the second compartment to increase 1 liter with a corresponding reduction in volume of the first compartment. Recovery of a further 20 liters NTP of gas to provide a container pressure of 2.5 bar would permit the remaining fresh gas (35 liters NTP) to be dispensed with the volume of the first compartment falling to 0 and the second compartment increasing to 10 liters (the volume of the container).

The processing apparatus may be any apparatus requiring a supply of gas in order to carry out a process.

In one embodiment, the processing apparatus is a cardiopulmonary bypass oxygenator or an artificial ventilator. There may be more than one processing apparatus, in which case there may be a cardiopulmonary bypass oxygenator and an artificial ventilator, the first gas being provided to either one or the other (or both) of the processing apparatus at any given time.

In an alternative embodiment, the processing apparatus is a gas separation or purification apparatus, in which cease the gas recovered from the processing apparatus is a purified gas.

The gas recovered from the processing apparatus may be removed to a remote location for disposal, purification or further use.

Preferably, at least a portion of the second gas, which preferably includes gas recovered from the processing apparatus, is a component of the first gas, the first gas having been through a process of the processing apparatus.

The recovered gas may be analyzed using an appropriate analyzer such that if the recovered gas meets at least one predetermined analyzed criterion, preferably a minimum content of a particular component, it is fed into the second compartment of the container. Otherwise, it may be vented to atmosphere or, as an alternative, recycled through the processing apparatus.

Alternatively, the recovered gas is fed into the second compartment of the container if it meets predetermined criteria in combination, such as when a minimum content of a particular component is present and where the minimum content set depends upon the pressure in the second compartment of the container. For example, when the pressure in the second compartment approaches its upper limit, the minimum content of a particular component of the recovered gas that would lead to it being fed into the second compartment is greater than when the pressure in the second compartment is lower and the second compartment thereby has a greater remaining capacity.

The recovered gas is preferably fed into the second compartment using a pump.

In a preferred embodiment of the invention, the pressure of gas in the second compartment is maintained above 1 atmosphere absolute (0.1 MPa). This should ensure that the entire content of the first compartment may be dispensed. Optionally, if the pressure of gas fails below a predetermined level, a check valve will open and allow a further gas (preferably compressed air) to be pumped into the second compartment until the pressure exceeds the predetermined level.

Preferably the first gas comprises a high value gas which it would be beneficial to recover after use in the process. Such a gas includes the noble gases, especially xenon, krypton and neon or isotopes thereof, or stable isotopes of gases such as oxygen and carbon dioxide.

In a preferred embodiment, the first gas comprises xenon, preferably in an amount of at least about 10% by volume, more preferably at least about 30%, still more preferably at least about 50% and most preferably at least about 70% by volume. Most preferably, the first gas comprises xenon in an amount of about 80% by volume.

The first gas preferably also comprises oxygen.

In a more preferred embodiment, the first gas consists predominantly of xenon and oxygen and preferably consists solely of xenon and oxygen. In a preferred embodiment, the first gas is a mixture of xenon and oxygen for dispensing to a ventilator and to a cardiopulmonary bypass oxygenator.

Preferably there should be sufficient volume of the first gas in the first compartment to fill the ventilator twice and the oxygenator once, plus an additional single fill for safety. The container should therefore contain up to 20 liters of xenon/oxygen mixture at a pressure of about 3 to about 4 atmospheres absolute (about 0.3 to about 0.4 MPa).

Preferably the second gas comprises xenon, preferably in an amount of at least about 5%, more preferably in an amount of at least about 10%, still more preferably in an amount of at least about 50% and most preferably about 70% by volume and especially about 80% by volume.

Preferably the container has a rigid housing and the partition is a flexible membrane, such as an inner lining or bag, which defines the first and second compartments where the second compartment is the ullage space in the container, outside defined between the housing and the membrane. For example, the container may comprise a flexible inner bag suitable for containing a first gas which is dispensed through the gas outlet via flow control means, e.g. a tap or valve, and the ullage space is charged through the gas inlet via, for example, a charging valve, with a gas recovered from the processing apparatus to which the first gas is fed or with a propellant gas such as compressed air.

Suitably, the container may be of the kind used in the brewing industry and described above, in which the container is a strong rubber or polypropylene outer jacket having a flexible internal membrane of, for example, heavy gauge metal foil with a dual plastic coating dividing the housing into the first and second compartments.

The apparatus and method of the present invention is particularly applicable with regard to the apparatus and method of our co-pending UK Patent Application No. 0210023.8 filed $1^{st}$ May 2002 and the corresponding PCT Patent Application of even date with the present application (file reference: P8944WO) in respect of a gas circulation apparatus.

The following is a description by way of example only and with reference to the accompanying drawings of presently preferred embodiments of the invention. In the drawings:—

Figure 1:
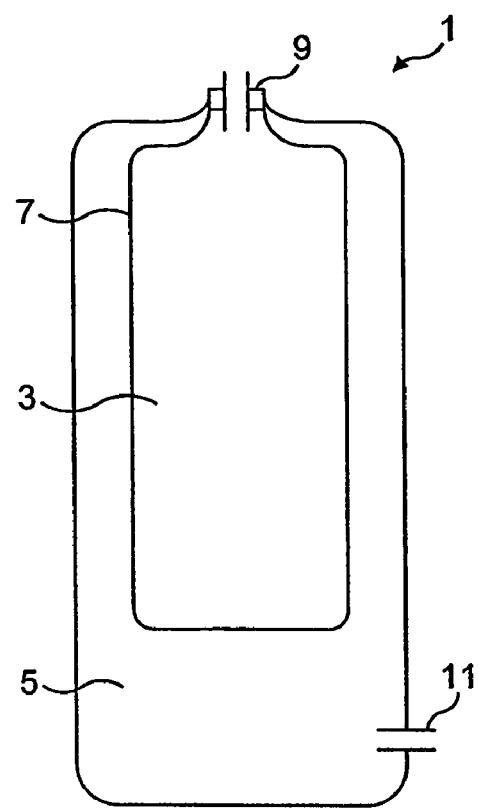
FIG. 1 is a cross-sectional side view of a gas cylinder for use in the present invention.

With reference to FIG. 1, a gas cylinder (generally designated 1) comprises a fresh gas space 3 defined by inner foil bag 7 and an ullage space 5 consisting of the remaining internal volume of cylinder 1. The contents of the fresh gas space 3 are accessed via dispensing valve 9 and the ullage space 5 is accessed via inlet valve 11.

Figure 2:
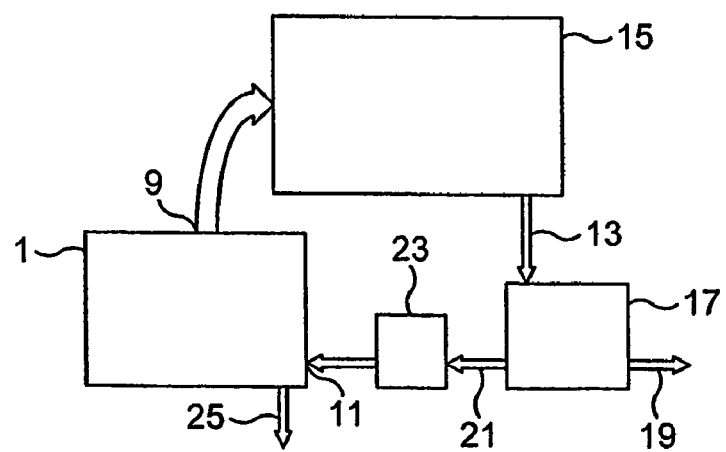
FIG. 2 is a schematic diagram of the gas container of FIG. 1 when attached to a process apparatus.

The fresh gas to be used is dispensed through valve 9 for use in the user's process apparatus 15 (see FIG. 2). Gas used in the process apparatus 15 is directed via used gas conduit 13 to analyzer 17. If the used gas does not reach a predetermined standard according to the analysis, it is vented through vent 19. If the predetermined standard is reached, the gas is directed through recovery conduit 21 and pump 23 pumps the recovered gas via inlet valve 11 into the ullage space 5.

The fresh gas in space 3 is provided at a lower pressure than pump 23 although the system is slightly pressured at all times to ensure complete evacuation of space 3 can be achieved. If desired, the initial pressure within the container can be such as to permit some recovery of gas into the ullage space prior to dispensing fresh gas. Dispensing and recovery can be continuous or discrete depending upon whether or not gas is recycled for use in the process apparatus 15.

Optionally a further check valve 25 is provided to ensure a minimum pressure is provided to the ullage space 5 ensuring that the pressure of gas in the ullage space does not fall below 1 atmosphere (0.1 MPa).

Figure 3:
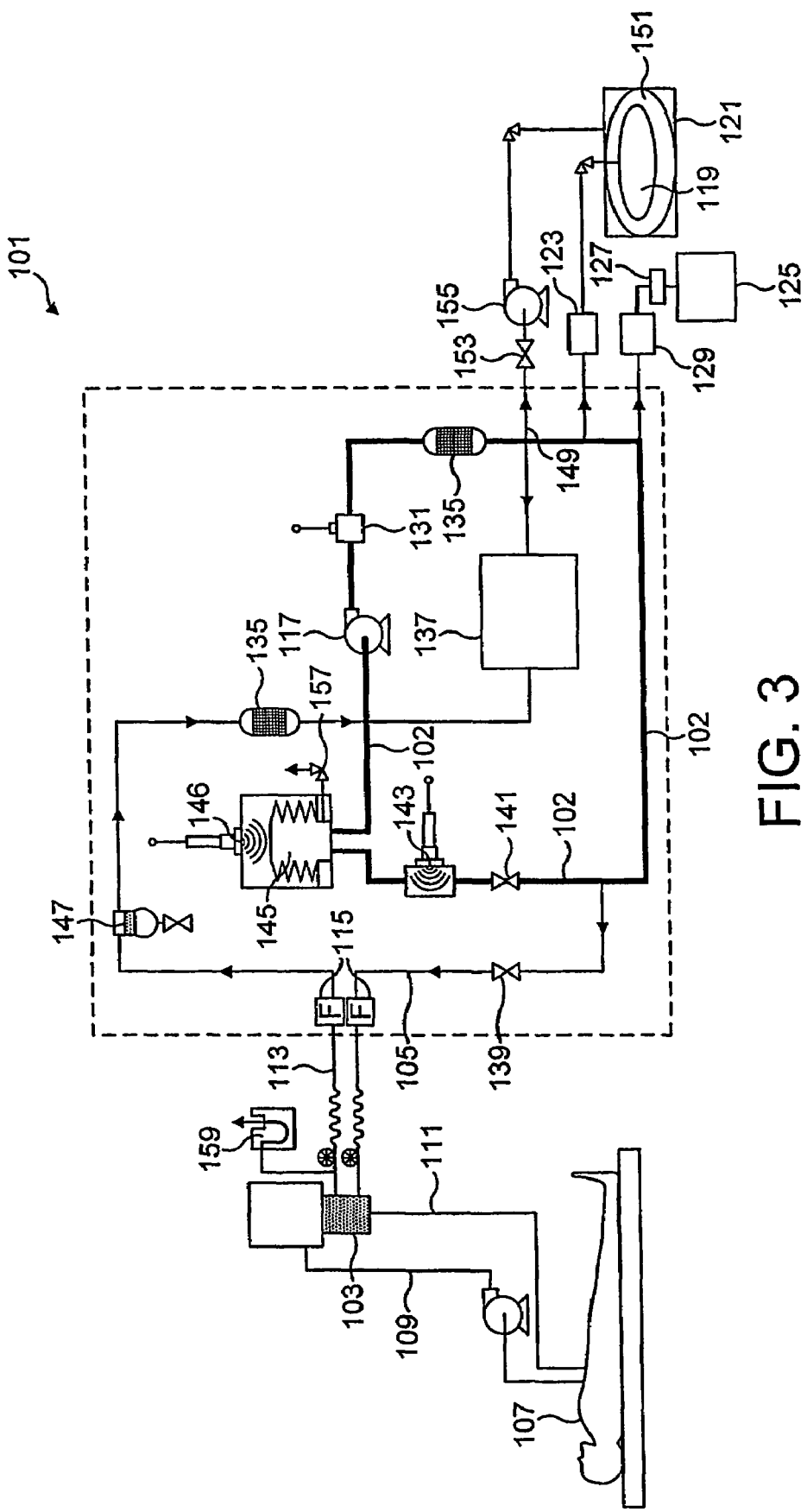
FIG. 3 is a diagrammatic representation of the use of gas container of FIG. 1 in a gas recirculation apparatus for providing gas to a cardiopulmonary bypass oxygenator.

With reference to FIG. 3, a xenon/oxygen mixture in a ratio of 80% xenon to 20% oxygen is fed into the main circuit 102 of the apparatus (generally designated 101) from a xenon/oxygen supply in fresh gas space 119 of container 121 via xenon mass flow controller (MFC) 123. Container 121 is as described above with reference to and illustrated in FIG. 1.

The oxygen content of main circuit 102 is topped up from oxygen cylinder 125 via regulator 127 and oxygen mass flow controller (MFC) 129.

One or more (preferably four) diaphragm pumps 117 pump the xenon/oxygen mixture around the circuit 102 at a rate of up to 20 liters per minute (l/min) at a pressure of up to 150 millibar gauge (115 kPa).

The gaseous composition is fed to cardiopulmonary bypass (CPB) oxygenator 103 via medical device supply conduit 105, which is regulated by flow control valve 139, which may be set at a desired level by the operator.

CPB oxygenator 103, which is typically a membrane oxygenator, is fed unoxygenated blood from a patient 107 via unoxygenated blood conduit 109 and returned to the patient 107 via oxygenated blood conduit 111. Spent gas from the CPB oxygenator 103 is fed through spent gas return conduit 113 and then through water trap 147, primary carbon dioxide absorber 135 to return to the main circuit 102 upstream of pump(s) 117.

Gas passing through the spent gas return conduit 113 and medical device supply conduit 105 pass through respective bacterial filters 115 to protect the patient 107 from contamination from the apparatus 101 and vice versa.

In order to ensure that a constant flow of gas at the set pressure is supplied to the oxygenator 103 and thus available to the patient's blood, gas circulates through the main circuit 102 via pressure maintaining valve 141 downstream from the outlet to medical device supply conduit 105. Pressure maintaining valve 141 is a valve which allows gas flow only when the pressure exceeds a predetermined level, for example 30 mbarg (103 kPa) and accordingly maintains a constant pressure between the pumps 17 and the valve 141.

Downstream from the pressure maintaining valve 141, the gaseous composition is analyzed for xenon content using ultrasonic xenon analyzer 143 of the kind described in our co-pending UK Patent Application No. 0210021.2 filed 1$^{st}$ May 2002 and the corresponding PCT Patent Application of even date with the present application (file reference P8942WO). In an alternative arrangement (not shown) the xenon analyzer is located upstream of the pressure maintaining valve 141.

The gas is then fed via bellows 145, which expand to take up any additional volume of gas in the apparatus or contract to compensate for loss of volume in the apparatus, and receives the spent gas upstream of pump(s) 117.

The oxygen concentration in the main circuit 102 is monitored by oxygen fuel cell sensor 131 that is shown situated in the main circuit 102 downstream from pump(s) 117 but could be located downstream of the pressure maintenance valve 141. The gas is then fed through backup carbon dioxide absorber 133, which removes residual carbon dioxide from the recirculating gas. The carbon dioxide removed by absorbers 133 and 135 has entered via the oxygenator 103 after being flushed from the patient's blood. At least absorber 135 should be replaced with each use of the system.

Downstream from the backup carbon dioxide absorber 133, a small sample of gas is drawn from the main circuit 102 and fed to analyzer unit 137 to be analyzed for carbon dioxide, via an infra red gas analyzer, to ensure that the carbon dioxide absorbers are working efficiently and for oxygen, via a paramagnetic gas analyzer, as a backup to the oxygen fuel cell sensor 131. The sample is returned to the main circuit 102 upstream from the pump(s) 117.

Recovery gas conduit 149 selectively feeds at least a portion of gas from the main circuit 102 at a point downstream from the backup carbon dioxide absorber 133 to the ullage space 151 of container 121, via recovery valve 153 and compressor 155.

An atmospheric vent 157 from bellows 145 enables the gas within the apparatus to be vented to atmosphere if desired.

There is a U-tube relief device 159 on the spent gas return conduit 113 to protect the oxygenator 103 and patient 107 in the event of any back pressure from the apparatus 101.

Addition of fresh gas to the apparatus is controlled by an analog electronic circuit (not shown) between oxygen fuel cell sensor 131 and oxygen MFC 129 for fresh oxygen addition and by an analog electronic circuit between an ultrasonic level sensor 146 measuring the position of the bellows and the xenon MFC 123 for fresh xenon/oxygen mixture addition.

As well as monitoring the concentration of oxygen in the main circuit 102, oxygen fuel cell sensor 131 enables the oxygen concentration to be controlled. The operator may choose a set point on the sensor 131 corresponding to the desired oxygen concentration. When oxygen concentration measured by sensor 131 falls below the set point, oxygen MFC 129 is triggered to feed fresh oxygen into the main circuit 102 at a rate proportional to the difference between the oxygen level set point and the oxygen sensor 131 measurement via a high gain circuit connecting oxygen MFC 129 to sensor 131.

Typically, the high gain oxygen control circuit (not shown) will have a gain of 1, corresponding to an oxygen flow rate through oxygen MFC 129 and into the main circuit 102 of 1 l/min for every 1% difference between the oxygen set point and the measured oxygen level.

The xenon concentration of the main circuit is controlled by ultrasonic bellows level sensor 146. The operator may set the desired level on a potentiometer (not shown) connected to sensor 146, which corresponds to an expanded level of the bellows 145. This level corresponds to the volume in the system and, given that the oxygen concentration is known, to a desired concentration of xenon. When the sensor 146 detects that the bellows 145 has fallen below the desired level, xenon MFC 123 is triggered to feed fresh oxygen/xenon mixture into the main circuit 102 at a rate proportional to the difference between the potentiometer set point and the level measured by bellows sensor 146, via a low gain circuit (not shown) connecting sensor 146 to xenon MFC 123.

Typically, the xenon low gain circuit will have a gain of 0.1, corresponding to a flow of fresh xenon/oxygen mixture into the main circuit 102 of 0.1 l/min for every 1% difference between the potentiometer setpoint and the level measured by bellows sensor 146.

The various sensor readings and flow rates are displayed on a monitoring unit (not shown).

In use, oxygen is consumed and replaced by carbon dioxide via the CPB oxygenator 103. The operator may select the flow rate to the oxygenator 103 by using flow control valve 139. This effectively controls the rate that carbon dioxide is flushed from patient's blood into the apparatus and hence provides some control as to the relative acidity or alkalinity of the patent 107.

Carbon dioxide is absorbed by primary carbon dioxide absorber 135 and the reduction in the oxygen level is detected by fuel cell sensor 131 triggering, via the high gain circuit, replenishment of oxygen levels under the control of oxygen MFC 129.

Xenon sensor 143 measures the xenon concentration in the main circuit 102. This reading may be compared to other readings to reach various conclusions. For example, if the oxygen concentration measured by oxygen fuel cell sensor 131 does not equal 100 minus the xenon concentration measured by xenon sensor 143, it is indicative of contamination, for example by carbon dioxide or nitrogen, and the operator may be alerted to vent the apparatus to atmosphere or recover the used gas. Alternatively, this may be done automatically at a preset level. The xenon sensor 143 is also used to monitor the xenon concentration predicted from the level of the bellows. Similarly, if these two readings do not agree, this may be indicative of too much carbon dioxide, nitrogen or oxygen. As a result, the operator may again choose to vent to atmosphere or recover the used gas.

If the gas volume in the apparatus is increased, the level of bellows 145 increases. If the level of bellows 145 exceeds a preset level, gas is vented from the apparatus, again either manually or automatically, via atmospheric vent 157 and/or xenon recovery valve 153. Optionally, the sensor 146 may be connected to ultrasonic analyzer 143 so that when the bellows 145 upper level is exceeded, vent 157 or valve 153 is selectively opened depending on the xenon content of the gas measured by analyzer 143.

Although illustrated and described herein with reference to certain specific embodiments, the present invention is nevertheless not intended to be limited to the details shown. Rather, various modifications may be made In the details within the spirit and scope of the following claims.

The invention claimed is:

1. A method of storing and dispensing a first gas for use in a process and receiving and storing a second gas, said method comprising the steps of storing the first gas in the first compartment of a container having a first compartment and a second compartment separated by a movable gas impermeable partition, dispensing the first gas from the first compartment via a gas outlet of the container and providing the first gas to a processing apparatus for carrying a process involving the first gas;

recovering gas from said processing apparatus; and feeding at least a portion of said recovered gas to the second compartment via a gas inlet of the container to provide at least a portion of the second gas, whereby a volume of the second gas displaces a volume of the first gas by movement of the partition to enlarge the second compartment relative to the first compartment.

2. The method of claim 1, wherein the container has a rigid housing with a flexible internal membrane dividing the housing into the first and second compartments.

3. The method of claim 1, wherein at least a portion of the second gas is a component of the first gas.

4. The method of claim 1, which further comprises the steps of analysing the recovered gas and feeding to the second compartment at least a portion of the recovered gas that satisfies at least one predetermined criterion determined by said analysis.

5. The method of claim 1, wherein the pressure of gas in the second compartment is maintained above 0.1 MPa (1 atmosphere).

6. The method of claim 1, wherein the first gas comprises a gas selected from the group consisting of noble gases, noble gas isotopes, isotopes of oxygen and isotopes of carbon dioxide.

7. The method of claim 1, wherein the first gas comprises xenon.

8. The method of claim 7, wherein the first gas comprises xenon in an amount of at least about 50% by volume.

9. The method of claim 7, wherein the first gas further comprises oxygen.

10. The method of claim 9, wherein the xenon and oxygen are the sole components of the first gas.

11. The method of claim 7, wherein the second gas comprises xenon.

12. The method of claim 1, wherein the processing apparatus is selected from the group consisting of cardiopulmonary bypass oxygenators and artificial ventilators.

13. An apparatus for storing and dispensing a gas for use in a process and receiving and storing a gas recovered from the process, said apparatus comprising a container, which container comprises a first compartment for containing a first gas and having a gas outlet;

a second compartment for containing a second gas and having a gas inlet;and a gas impermeable partition which separates the first compartment and the second compartment and is moveable such as to enable the relative volumes of the first and second compartments to be varied;

a processing apparatus for carrying out a process involving a gas;

a dispensing conduit for feeding gas from the gas outlet to the processing apparatus;

a recovery conduit for feeding gas from the processing apparatus to the gas inlet; and a pumping means for pumping the gas from the processing apparatus into the second compartment.

14. The apparatus of claim 13, wherein the container has a rigid housing with a flexible internal membrane dividing the housing into the first and second compartments.

15. The apparatus of claim 13, wherein the processing apparatus is an artificial ventilator.

16. The apparatus of claim 13, wherein the processing apparatus is a cardiopulmonary bypass oxygenator.

* * * * *

UNITED STATES PATENT AND TRADEMARK OFFICE
CERTIFICATE OF CORRECTION

PATENT NO.        : 7,431,033 B2                                          Page 1 of 1
APPLICATION NO.   : 10/512734
DATED             : October 7, 2008
INVENTOR(S)       : Neil Alexander Downie and Stuart Alexander Kerr It is certified that error appears in the above-identified patent and that said Letters Patent is hereby corrected as shown below:

Column 7, Line 42

In claim 1 insert -- out -- after the word carrying

Signed and Sealed this

Sixteenth Day of December, 2008

JON W. DUDAS
*Director of the United States Patent and Trademark Office*